United States Patent [19]

Raleigh et al.

[11] Patent Number: 5,086,068

[45] Date of Patent: Feb. 4, 1992

[54] IMMUNOCHEMICAL DETECTION OF HYPOXIA IN NORMAL AND TUMOR TISSUE

[75] Inventors: James A. Raleigh; Gerald G. Miller; Allan J. Franko; J. D. Chapman, all of Edmonton, Canada

[73] Assignee: Alberta Cancer Board, Edmonton, Canada

[21] Appl. No.: 161,034

[22] Filed: Feb. 26, 1988

[51] Int. Cl.$^5$ .................. A61K 31/415; A61K 37/00; A61K 31/70; A61K 31/20

[52] U.S. Cl. .......................... 514/398; 514/2; 514/23; 514/44; 514/558; 536/1.1; 536/27

[58] Field of Search ............. 514/398, 885, 44, 23, 514/2, 558; 536/27, 1.1

[56] References Cited

U.S. PATENT DOCUMENTS 4,241,060 12/1980 Smithen .......................... 514/212
4,282,232 8/1981 Agrawal ........................... 514/326

OTHER PUBLICATIONS

Chem. Abst. 11(1): 223k, 1989.
Chem. Abst. 101:71201f and 71202g, 1984.
Chem. Abst. 100:132082w, 1984.
Chem. Abst. 79:27794e, 1973.
Chapman (1979), New England J. Med., 301:1429-1432.
Urtasun, et al., (1986), British Journal of Cancer, 54:453.
Whillians, (1981) Radiation Research, 86:311.
Fuciarelli, et al., (1985) Radiation Research, 104:272.
Franko, (1985) Radiation Research, 103:89.
Franko, et al., (1984) Recent Res. Cancer Res., 95:162.
St. Marie, (1962) J. Histochem. Cytochem., 10:250.
Raleigh et al., (1987) British Journal of Cancer, 56:395-400.

*Primary Examiner*—John W. Rollins
*Attorney, Agent, or Firm*—Banner, Birch, McKie & Beckett

[57] ABSTRACT

A process for preparing an immunogenic conjugate of a nitroaromatic compound and a carrier comprises colavently bonding the nitroaromatic compound to the carrier in an essentially oxygen-free atmosphere and isolating the conjugate from the reaction mixture. The conjugate may be used to raise antibodies specific to the nitroaromatic hapten. The antibodies may be used to determine the presence of hypoxic tissue in living matter by treating the living matter with a nitroaromatic compound and subsequently testing suspected tissue to determine if there is binding of the antibody to tissue. By use of appropriate markers, bound antibodies can be determined to indicate the presence of hypoxic tissue due to the unique reaction of nitroaromatic compounds with hypoxic tissue.

15 Claims, No Drawings

IMMUNOCHEMICAL DETECTION OF HYPOXIA IN NORMAL AND TUMOR TISSUE

FIELD OF THE INVENTION

This invention relates to the detection of hypoxic cells in living tissue, such as may be found in tumors and the development of antibodies for use in such determination.

BACKGROUND OF THE INVENTION

It has been known for some time that nitroaromatic compounds will bind to hypoxic cells in living matter. Hypoxic cells are those that are deficient in oxygen, yet remain viable. Hypoxic cells are most commonly found in tumors; however, it is understood that such cells may also exist in other living tissue, for example, heart tissue of a heart having undergone cardiac arrest or that has suffered the consequences of a stroke.

With specific reference to cancerous tissue, as tumors enlarge, the tumor tissue often outgrows its supply of oxygen and nutrients, because of an inadequate network of functioning blood vessels and capillaries. Although cells deprived of oxygen and nutrients ultimately die, at any given time a tumor may possess viable hypoxic cells; i.e., those cells which are deficient in oxygen, but are still functioning.

Radiation treatment is commonly used to destroy tumors. It has been determined that the rate of killing by radiation is 2.5 to three times higher for cancerous cells which contain oxygen than cancerous cells which are hypoxic. Hence hypoxic cells are more likely to survive radiation therapy and because they remain viable, eventually lead to the reappearance of the tumor. Chapman discusses this problem in "Current Concepts in Cancer", The New England Journal of Medicine, 304: 1429-1432, Dec. 27, 1979. There is at present, however, no practical and generally useful way of estimating the extent of hypoxia in a given tumor in a particular patient. On the other hand, if a measure of hypoxia were available, there are therapeutic interventions which can be designed to deal with the presence of hypoxic cells in the treatment of the tumors.

It has been known since about 1970 that certain nitroaromatic compounds will metabolically bind to hypoxic cells. A variety of techniques have been developed based on this discovery to determine the presence of hypoxic cells in living tissue. The clinically viable way of positively identifying and quantifying hypoxic tissue in tumors is by the use of radioactively labelled 2-nitroimidazoles. The reactive chemical is injected into tumor bearing animals or humans. The excess chemical is allowed to wash out and biopsy samples are investigated by scintillation, counting and autoradiography. This technique is disclosed in more detail by Urtasun et al, 1986, "A Novel Technique for Measuring Human Tissue $pO_2$ at the Cellular Level", Br. J. Cancer, 54, 453. This approach can provide important information on the degree of tumor hypoxia, but is not generally acceptable because of the stringent requirements associated with handling radioactive tissues and body fluids. The delay required for autoradiographic analysis of the tissue sections is also a limitation with respect to the treatment plan. Nevertheless, the studies with radioactively labelled drug have established the usefulness and feasibility of the overall concept.

Agrawal, U.S. Pat. No. 4,282,232, discloses nitroimidazoles useful in radio-sensitizing hypoxic cells. The compounds are administered at acceptable levels to sensitize hypoxic cells such that, when treated with radiation, the now more sensitive hypoxic cells are killed. A further example of the use of nitroimidazoles in this manner is disclosed in U.S. Pat. No. 4,241,060.

The methodology, according to this invention, provides a technique for estimating the degree of hypoxia in tumors by existing medical laboratories which can be carried out in the same manner as other standard histochemical analyses of tumor tissue. Quick feedback is then provided by this invention so that adjustments in the treatment may be taken to deal with the hypoxic cells without any concern for radioactively labelled materials.

SUMMARY OF THE INVENTION

According to an aspect of the invention, a process for preparing an immunogenic conjugate of a nitroaromatic compound covalently bonded to an immune response inducing carrier comprises covalently bonding the nitroaromatic compound to the carrier in an essentially oxygen-free atmosphere. The formed conjugate is then isolated.

According to another aspect of the invention, an immunogenic conjugate comprises a nitroaromatic compound covalently bonded to an immune response inducing carrier. The conjugate is used to raise antibodies specific to the nitroaromatic hapten.

According to another aspect of the invention, the raised antibodies are used to detect the presence of hypoxic tissue in living matter by virtue of a nitroaromatic compound, to which the antibodies are specific, being metabolically bound with the hypoxic tissue. The presence of bound antibody may be determined in accordance with standard practice.

DETAILED DESCRIPTION OF THE PREFERRED EMBODIMENTS

According to this invention, an immunochemical method is provided for detecting hypoxic tissue and cells in tumors and other living matter. For purposes of discussion and demonstration of the invention, preferred aspects of the invention will be discussed with regard to the detection of hypoxic tissue and cells in tumors. Although it is understood that hypoxic tissue, as it may occur in living matter that has been subject to a heart attack or stroke, can also be detected by this invention. The methodology of this invention provides a relatively simple test to detect the extent of hypoxic tissue in a tumor or the like so that the treatment for the tumor by radiation can be adjusted at the onset and during the course of treatment. Although it is recognized that nitroaromatic compounds and in particular 2-nitroimidazoles metabolically bind preferentially to hypoxic tissue rather than normally healthy oxygen-rich tissue, the only viable attempt to use this information in identifying hypoxic tissue has been to rely on raadioactively labelled nitroaromatics which are administered to the patient. Radioactivity is a known biohazard and the use of radioactively labelled drugs is a very difficult issue.

In accordance with this invention, advantage has been taken of the concept that nitroaromatic compounds selectively bind metabolically to hypoxic tissue to develop in vitro a conjugate which can be used to raise antibodies specific to the nitroaromatic hapten of the conjugate. Hence, the conjugate of this invention attempts to mimic chemically in test tubes the in vivo metabolic binding of nitroaromatic compounds to macromolecules of hypoxic cells. It has been discovered that nitroaromatic compounds covalently bound to a suitable carrier in an oxygen-free atmosphere will act as a hapten and can be used to develop antibodies specific to the hapten of the conjugate. The nitroaromatic compound must, however, be bound to the carrier in a oxygen-free atmosphere in providing the reductive covalent binding. The carrier may be any suitable immunogenic macromolecule, such as a protein, deoxyribonucleic acid, ribonucleic acid, a lipid or a carbohydrate. The formed conjugate may then be isolated from the reaction mixture.

The preferred technique in covalently binding the nitroaromatic compound to the carrier is to irradiate a mixture of nitroaromatic compound having a concentration of approximately 10 to 1000 micromolar and the selected carrier, which may be a protein or other suitable immunogenic macromolecule, at a concentration of 0.1 to 1.5 mg/ml in the presence of 50 to 200 mmolar sodium formate in a 50 mmolar phosphate buffer having a pH of 4 to 9. The reaction is carried out in the absence of oxygen. The irradiation of the mixture provides for the reductive activation of the nitroaromatic compound to produce a reactive intermediate which binds to the carrier. The electrons required for the reductive covalent binding in the reaction mixture are produced by the radiolysis of water. When ionizing radiation, such as gamma rays or x-rays, is absorbed by the water molecules, the water molecules are split into electrons ($e^-aq$) hydroxyl radicals (OH) and protons ($H^+$). This aspect of the process can be outlined by the following formula:

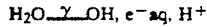      I

The hydroxyl radical can be used to increase the reducing power of the aqueous solution by scavenging it with molecules such as the sodium formate ($HCOO^-Na^+$) or isopropanol [$(CH_3)_2CHOCH$]. Such scavenging is exemplified in the following formulas:

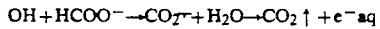      II

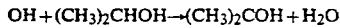      III

Any of the above species $e^-aq$, $CO_2^-$ or $(CH_3)_2\dot{C}OH$ can give up electrons to a nitroaromatic compound dissolved in the irradiated solution to reduce it to the reactive hydroxylamine or related intermediate which binds to the protein. In this manner, a conjugate can be prepared in vitro which has been found to be very useful in developing the necessary antibodies for detection of nitroaromatic compounds metabolically bound to hypoxic tissue in living matter.

In forming the hapten-carrier conjugate in vitro, it is understood that techniques other than reductive binding can be used, although the binding is still carried out in an oxygen-free atmosphere. For example, the binding may be accomplished by chemical reductants, enzymes, subcellular fractions or whole cells. Oxidative binding of the nitroaromatic is also useful in forming the conjugate.

According to a preferred aspect of the invention, particularly useful nitroaromatic compounds, which function as the hapten in the conjugate, are 1-(2-hydroxy-3-hexafluoroisopropoxy-propyl)-2-nitroimidazole, 1-[2-hydroxy-3-(2,2,2-trifluoroexthoxy)-propyl]-2-nitroimidazole and 1-(2-hydroxy-3-methoxy-propyl)-2-nitroimidazole. These compounds are represented by the formulas:

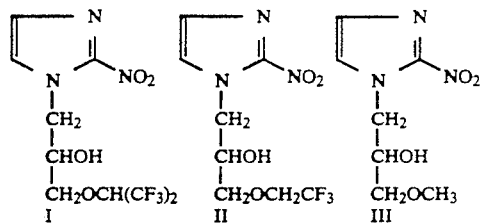

A variety of well known carriers are available which, when used in a conjugate, effect an immune response in the system in which antibodies are being raised. Suitable carriers include bovine serum albumin (BSA), and *Limulus polyphemus* hemolymph Type VIII (haemocyanin). The preferred type of haemocyanin can be purchased from Sigma Chemical Company.

Once the conjugate is isolated from the reaction mixture by gel filtration, chromatography, extensive dialysis or the like, the conjugate may then be used to raise antibodies to the selected hapten. It is appreciated that polyclonal antibodies or monoclonal antibodies may be prepared for subsequent use in confirming the presence of hypoxic tissue which has metabolically bound the nitroaromatic compound selected as the hapten. Polyclonal antibodies may be raised by injecting a suitable host with the conjugate to elicit an immune response in the host and hence prepare antibodies to the conjugate. After a suitable period, blood is collected from the host and purified to provide an antisera or provide for a recovery of the polyclonal antibodies from the antisera. Monoclonal antibodies can also be prepared by standard hybridoma technique. A hybridoma is prepared which produces the appropriate monoclonal antibody to the conjugate. The monoclonal antibody is then isolated from the cultured hybridoma.

As previously noted, the administration of a selected nitroaromatic compound to an animal results in the selective metabolic binding of the nitroaromatic compound to hypoxic tissue if it is present in living tissue. The specific binding is thought to be due to the presence of an enzyme whose normal properties are subverted to that of nitroreductase when the tissue is deprived of oxygen and the nitroaromatic compounds happen to be present in the tissue. Hence intentionally introducing a nitroaromatic compound to a tumor bearing patient results in the nitroreductase activity binding the nitroaromatic compound to the hypoxic tissue. This aspect of the preferential binding of nitroaromatic compounds to hypoxic tissue has previously been investigated, such as disclosed in Urtasun et al, Br. J. Cancer, 54: 453–457, 1986. In accordance with this invention, at a predetermined time prior to analysis of a tumor, for example 20 hours prior to surgical inspection of the tumor, the tumor bearing animal or patient is injected with a whole body concentration of approximately 5 to 50 micromolar nitroaromatic compound. A biopsy sample of the patient tumor is taken for purposes of investigation by use of the antibodies developed by this invention. The nitroaromatic compound, as administered to the patient, is the same nitroaromatic compound which is used as the hapten in developing the antibody.

As a general overview of the process, the biopsy sample of the tumor may be fixed with cold ethanol in the range of −20° C. or with formaldehyde and embedded in paraffin. Sections of approximately 2 to 4 μm in thickness are deparaffinized, hydrated through an alcohol series and rinsed in phosphate buffered saline (PBS) at a pH of 7.2. The samples are then incubated at 4° C. with the antibody reagent which may be the developed antisera and which recognizes the nitroaromatic compound bound to the macromolecules in the cells of the hypoxic tissue. After suitable preparation, the sample is incubated for one hour at 37° C. in the presence of another fluorescent labelled antibody which is capable of recognizing the first antibody. The sample is then recovered and observed in a suitable fluorescence microscope to determine whether or not any of the developed antisera is present. If fluorescence occurs, then this confirms the presence of hypoxic tissue, due to the nitroaromatic compound having bound to hypoxic tissue in the tumor. In this technique, it is appreciated that hypoxic tissues and cells may be labelled directly using the first antibody as developed by use of the conjugate. Labelling of the primary antibody with a fluorescent chromophor, for example, is done in a manner to ensure compatibility with the animal during use. It is also appreciated that alternatives to the use of a fluorescent label on the first or second antibody may be used. Such alternatives include chromogenic labelling for use in immunohistochemical assays; e.g. peroxidase/chromogen couple, electron microscope variations; e.g., ferritin-labelled second antibody and the use of biotin/avidin modifications.

It is appreciated that a variety of nitroaromatic compounds may be used. Such useful nitroaromatic compounds may be generally selected from the group of compounds consisting of nitrobenzenes, nitrofurans, nitrothiazoles, nitropyrroles, nitrodiazoles and nitrotriazoles. As noted, the ring structure of the nitroaromatic compound must include $-NO_2$ group. This provides a site at which reduction takes place to provide an hydroxylamine derivative or related intermediate which can bind with the carrier. In instances where the carrier is a protein, the hydroxylamine intermediate is bound to protein sulfhydryl and amino groups.

Preferred aspects of the invention are demonstrated in the following Examples in the making of the conjugate, use of the conjugate to raise antibodies and use of the raised antibodies to identify hypoxic tissue in living matter. It is understood that the Examples are not to be interpreted in a limiting way with regard to the scope of the invention as defined in the appended set of claims. For purposes of demonstrating aspects of the invention, suitable tumor cells in the form of spheroids were cultured to the extent to provide hypoxic cells within the spheroids. For purposes of discussion, the conjugate 1-(2-hydroxy-3-hexafluoroisopropoxypropyl)-2-nitroimidazole is identified in the Examples as CCI-103F. Other short forms as used in the Examples are self-explanatory and of nomenclature well understood by those skilled in the art.

EXAMPLE 1—Immunogens

For the purpose of raising antibodies, CCI-103F was reductively bound to haemocyanin by an adaptation of a radiation chemical reduction method (Whillans, D. W. and Whitmore, G. F. (1981) "The Radiation Reduction of Misonidazole", Radiat. Res. 86: 311). CII-103F (8.4 mg) was dissolved in 25 ml of 0.1 mol.dm$^{-3}$ aqueous isopropanol (pH 3.0). Haemocyanin (25 mg) was added to the solution which was then deaerated in a gassing manifold in a manner similar to that described below for the deoxygenation of multicellular spheroids. The deaerated solution was irradiated to a dose of $10^4$ Gy at a dose-rate of 28 Gy min$^{-1}$. This dose was sufficient to completely reduce the nitro group in CII-103F as measured by ultraviolet spectroscopy at 320 nm. The irradiated solution was placed in a dialysis membrane and dialyzed extensively against 0.14 mol.dm$^{-3}$ CaCl, 1.5 mmol.dm$^{-3}$ KH$_2$PO$_4$, 8 mmol.dm$^{-3}$ Na$_2$HPO$_4$, 3 mmol.dm$^{-3}$, KCl, pH 7.4 (PBS) to remove unbound CCI-103F. The dialyzed solution was concentrated in vacuo to 7.0 ml in a rotary evaporator (40° C.). The haemocyanin may clump during this procedure and the suspension should be sonicated before being divided in 1.0 ml aliquots and stored at −17° C. A bovine serum albumin (BSA) conjugate with reductively activated CCI-103F was also prepared for use in the characterization of antisera to CCI-103F by enzyme-linked immunosorbent assay (ELISA).

EXAMPLE 2—Immunization and Treatment of Antisera

Two Flemish Giant x Lop-ear rabbits (one male, one female) were injected by the haemocyanin-CCI-103F conjugate. Prior to the initial immunization, 20 ml of blood were collected from the ear vein of each rabbit. These preimmune serum samples were used as control sera in subsequent assays. Each rabbit received a total of 0.4 ml of the antigen (3.6 mg protein ml$^{-1}$) emulsified with an equal volume of Freund's complete adjuvant injected at multiple subscapular sites. Similar booster injections emulsified in Freund's incomplete adjuvant were administered by the same route on days 21, 42 and 63. Sera (10 ml) were collected on days 21, 42 and 63. Immediately following collection, the blood was allowed to clot, the serum was drawn off and centrifuged twice. Aliquots of 0.5 ml were stored at −17° C.

EXAMPLE 3—ELISA Methodology

The sera of Example 2 were characterized by the well known ELISA methods (described previously) including reagent dilution assay and competitive inhibition assay [Fuciarelli et al (1985) "An Immunochemical Probe for 8,5'-cycloadenosine 5'-monophosphate and its Deoxy Analogue in Irradiated Nucleic Acids", Radiat. Res. 104: 272]. The extent of color development from the alkaline phosphatase substrate (Sigma 104 phosphate substrate) was recorded using an EL 309 Microplate Autoreader at 410 nm.

EXAMPLE 4—Spheroid Culture

Spheroids of EMT6/Ed tumor cells were cultured following procedures that have been published [Franko, A. J. (1985) "Hypoxic Fraction and Binding of Misonidazole in EMT/6Ed Multicellular Tumor Spheroids" Radiat. Res. 103: 89]. Briefly, spheroids were initiated in non-tissue culture dishes (Lab Tek), to which the cells do not adhere. After an initial aggregation into clumps of 10 to 50 cells, the spheroids grew by cell proliferation. When they reached a diameter of 0.4 to 0.6 mm, they were transferred to 250 ml spinner flasks (O. H. Johns). After a lag phase of 2 to 3 days, the spheroids grew 0.1 mm day$^{-1}$. On the fourth day in spinner flasks, spheroids of 0.8±0.05 mm were selected and returned to the flasks at a density of one spheroid per 2 ml medium. The growth medium, Waymouth's with 12% fetal calf serum (Gibco) was replenished daily. The spheroids were used on the eighth day in spinner flasks, when their diameters were 1.2±0.1 mm. The flasks were flushed continuously with humidified air—5% $CO_2$ at 0.1 mm$^{-1}$ for 2 days prior to use of the spheroids.

EXAMPLE 5—Incubation of Spheroids with Misonidazole and CCI-103F

In an experiment designed to compare the binding of misonidazole and CCI-103F, labelling of the spheroids with [$^3$H]-misonidazole (2.89 TBq mol$^{-1}$) was performed in the original growth flasks. For incubation in air, the drug was added in 0.2 ml medium to a final concentration of 0.10 mmol.dm$^{-3}$. For incubation at low oxygen, the flasks were flushed with $N_2$—5% $CO_2$ for 1.5 hours before the drug was added. This procedure results in an oxygen concentration equal to that in medium equilibrated with $N_2$—5% $CO_2$—0.13% $O_2$ [Franko et al (1984) "Oxygen Supply to Spheroids in Liquid Overlay and Spinner Culture", Recent Res. Cancer Res. 95: 162]. Three hours after the drugs were added, the spheroids were rinsed several times with PBS and processed for autoradiography.

For incubation with non-radioactive CCI-103F in the fluorescence immunohistochemical studies, the spheroids were transferred with 20 mmol.dm$^{-3}$ HEPES buffer (Gibco) to glass petri dishes containing 5.5 ml of Waymouth's medium. A separate growth flask was used for each of the two incubation conditions. The dishes were placed inside aluminium chambers fabricated with a removable base which forms a leakproof seal (via an O-ring) upon reassembly. The chambers were degassed to an oxygen content (0.0005%) which is much lower than that achieved in spinner flasks. The chambers were kept at 0° C. during the degassing, then placed in a 37° C. environmental chamber on a reciprocating table (1.1 Hz, 3 cm travel) for 3.5 hours. The dishes warmed to 37° C. in 30 minutes. After incubation, the spheroids were rinsed several times in PBS and processed for histochemistry. Incubation in air under these conditions might alter the oxygen supply to the spheroids somewhat from that present in spinner flasks. However, this was not deemed an important factor in the qualitative comparison reported here for the results obtained with autoradiography and fluorescence immunohistochemistry.

EXAMPLE 6—Autoradiography and Grain Scoring

The spheroids were dehydrated, embedded in wax and sectioned at 4 μm. The slides were dipped in NTB-2 Nuclear Track Emulsion (Kodak) and exposed for 5 days. The emulsion was developed, fixed and dried, then the sections were stained with haemotoxylin and eosin. The sections, which passed through the centers of the spheroids, were determined and these were used for scoring the grain density. An ocular grid with 10 μm squares at an overall magnification of 1000 times was positioned along a spheroid radius perpendicular to the direction of sectioning (to minimize the effects of distortion resulting from compression during sectioning) and grains were recorded as a function of distance from the spheroid surface. The grain densities along 13 to 18 radii from nine different spheroids were averaged for each incubation condition.

EXAMPLE 7—Histochemistry

EMT6/Ed spheroids were fixed in −20° C. ethanol [Sainte-Marie, G. (1962) "A Paraffin Embedding Technique for Studies Employing Immunofluorescence", J. Histochem. Cytochem., 10: 250] and embedded in paraffin. Sections (2-4 μm) were deparaffinized, hydrated through an alcohol series and rinsed in PBS, pH 7.2, prior to overnight incubation at 4° C. in rabbit anti-CCI-103F serum diluted 1:50 in the same buffer. Following extensive rinsing in PBS, the sections were incubated for one hour at 37° C. in rhodamine-conjugated, goat-antirabbit IgG (Cappel, Cooper Biomedical). Negative controls included substitution of the primary antibody with non-immune rabbit serum diluted 1:50 in PBS, or of the standard staining procedure of sections of multicellular spheroids which had not previously been incubated with CCI-103F. The tissue sections were rinsed and coverslipped with PBS-glycerol, 9:1 and observed with a Leitz Laborlux 12 microscope fitted with an HBO 50 W mercury burner and IVF1 epifluorescence condenser. Rhodamine was visualized with an interference green filter combination BP 530-560 and RKP 580 beam splitter. Fluorescence microphotographs were made using equal exposure times for each experimental parameter, the time being dependent upon the objective lens and film speed.

EXAMPLE 8—Labelling of Walker 256 Tumors with CCI-103F

Walker 256 tumors were initiated by subcutaneous implantation of frozen stock in the flanks of Sprague Dawley rats. Ten days after implantation, a rat with two tumors 1.5 to 2.0 cm in diameter was injected i.p. with 20 mg of CCI-103F in 20 ml of sterile saline, giving a whole body concentration of 200 μM. The tumors were excised 24 hours after the injection and fixed for 2 hours in −20° C. ethanol, then embedded in wax on the same day. Sections were obtained at 4 μm and processed for immunohistochemistry following the procedures that were used for the spheroid sections.

The specificity of the anti-serum was tested to ensure that it was specific to the compound CCI-103F. Such testing indicated that the fluorinated side chain of the compound is the major antigenic determinant in raising of the antibodies.

Sections of spheroids, which have been incubated with the CCI-103F compound in the absence of oxygen, showed a uniform fluorescence intensity from the surface of the spheroid inward to the edge of the nacrotic centre. On the other hand, spheroids incubated in air saturated medium containing the CCI-103F demonstrated increasing fluorescence intensity near the inner edge of the rim of the viable cells, thereby indicating the specific nature of the nitroaromatic compound metabolically binding to the hypoxic cells.

The selection of the nitroaromatic compound to be administered is such to ensure low toxicity to the patient and provide sufficient metabolic binding such that the corresponding raised antibody can bind to the nitroaromatic compound to indicate the presence of hypoxic tissue. The selected nitroaromatic compound may be administered in a variety of acceptable ways, such as by injection, tablet or liquid form. The concentration of compound administered will vary depending upon body weight. The preferred range of administration is 0.1 to 1.0 gm/m$^2$.

The embodiments of the invention in which an exclusive property or privilege is claimed are defined as follows:

1. A process for preparing an immunogenic conjugate of a nitroaromatic compound covalently bonded to an immune response inducing carrier, said process comprising covalently bonding a nitroaromatic compound selected from the group consisting of nitrobenzenes, nitrofurans, nitrothiazoles, nitropyrroles, nitrodiazoles and nitrotriazoles, each of said nitroaromatic compounds having a side chain including an $-NO_2$ group, to said carrier in an essentially oxygen-free atmosphere and isolating said conjugate.

2. A process of claim 1, wherein said nitroaromatic compound is covalently bonded by reductive binding to said carrier.

3. A process of claim 1, wherein said reductive binding is effected by reducing said nitroaromatic compound using a chemical reducing agent, ionizing radiation, or reducing enzyme.

4. A process of claim 1, wherein said carrier is a protein, said nitroaromatic compound is reduced to include an hydroxylamine group which is covalently bonded to a sulfhydryl group of said protein.

5. A process of claim 1, wherein said nitroaromatic compound is selected from the group consisting of nitrobenzenes, nitrofurans, nitrothiazoles, nitropyrroles, and nitrotriazoles, each of said nitroaromatic compounds having a side chain including an $-NO_2$ group.

6. A process of claim 1, wherein said nitroaromatic compound is a 2-nitroimidazole.

7. A process of claim 6, wherein said 2-nitroimidazole is 1-(2-hydroxy-3-hexafluoroisopropoxy-propyl)-2-nitroimidazole, 1-[2-hydroxy-3-(2,2,2-trifluoroethoxy)-propyl]-2-nitroimidazole or 1-(2-hydroxy-3-methoxypropyl)-2-nitroimidazole.

8. A process of claim 1, wherein said carrier is selected from the group consisting of proteins, deoxyribonucleic acid, ribonucleic acid, carbohydrates and lipids.

9. A process of claim 1, wherein said carrier is hemocyanin.

10. A process of claim 1, wherein said nitroaromatic compound is in solution at a concentration ranging from 10 to 1000 μmolar, and said carrier is at a concentration of 0.1 to 1.5 mg/ml.

11. A process of claim 10, wherein said solution includes 50 to 200 mmolar phosphate buffer at a pH ranging from 4 to 9.

12. A process of claim 3, wherein said nitroaromatic compound is a 2-nitroimidazole and said carrier is hemocyanin, reducing said 2-nitroimidazole in solution by radiating said solution with an ionizing radiation to produce electron donor components in solution which reduce said 2-nitroimidazole for covalent bonding to said hemocyanin.

13. A process of claim 12, wherein said 2-nitroimidazole is 1-(2-hydroxy-3-hexafluoroisopropoxy-propyl)-2-nitroimidazole, 1-[2-hydroxy-3-(2,2,2-trifluoroethoxy)propyl]-2-nitroimidazole or 1-(2-hydroxy-3-methoxypropyl)-2-nitromidazole.

14. An immunogenic conjugate comprising a nitroaromatic compound covalently bonded to an immune response inducing carrier, said nitroaromatic compound selected from the group consisting of nitrobenzenes, nitrofurans, nitrothiazoles, nitropyrroles, 2-nitroimidazoles and nitrotriazoles, each of said nitroaromatic compounds having a side chain including an $-NO_2$ group.

15. An immunogenic conjugate of claim 14, wherein said carrier is selected from the group consisting of proteins, deoxyribonucleic acid, ribonucleic acid, carbohydrates and lipids.

* * * * *